(12) United States Patent
Joy et al.

(10) Patent No.: US 9,663,614 B2
(45) Date of Patent: May 30, 2017

(54) PHOTORESPONSIVE COUMARIN BASED POLYMERS: SYNTHESIS AND APPLICATIONS

(71) Applicants: Abraham Joy, Copley, OH (US); Murthy V. S. N. Maddipatla, Louisville, KY (US)

(72) Inventors: Abraham Joy, Copley, OH (US); Murthy V. S. N. Maddipatla, Louisville, KY (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 14/440,645

(22) PCT Filed: Nov. 8, 2013

(86) PCT No.: PCT/US2013/069190
§ 371 (c)(1),
(2) Date: May 5, 2015

(87) PCT Pub. No.: WO2014/074845
PCT Pub. Date: May 15, 2014

(65) Prior Publication Data
US 2015/0274885 A1 Oct. 1, 2015

Related U.S. Application Data

(60) Provisional application No. 61/723,849, filed on Nov. 8, 2012.

(51) Int. Cl.
| | | |
|---|---|---|
| C07D 311/08 | (2006.01) |
| C08F 24/00 | (2006.01) |
| C08G 63/60 | (2006.01) |
| C07D 311/18 | (2006.01) |
| C08G 18/48 | (2006.01) |
| C08G 18/65 | (2006.01) |
| C08G 18/67 | (2006.01) |
| C08G 18/32 | (2006.01) |
| A01N 25/34 | (2006.01) |
| A61K 8/11 | (2006.01) |
| A61K 9/48 | (2006.01) |
| A61L 27/18 | (2006.01) |
| A61Q 19/00 | (2006.01) |
| C05G 3/00 | (2006.01) |
| G03F 7/038 | (2006.01) |

(52) U.S. Cl.
CPC ............. C08G 63/60 (2013.01); A01N 25/34 (2013.01); A61K 8/11 (2013.01); A61K 9/4816 (2013.01); A61L 27/18 (2013.01); A61Q 19/00 (2013.01); C05G 3/0017 (2013.01); C05G 3/0029 (2013.01); C07D 311/18 (2013.01); C08G 18/3206 (2013.01); C08G 18/4854 (2013.01); C08G 18/6511 (2013.01); C08G 18/6705 (2013.01); G03F 7/038 (2013.01); A61L 2430/02 (2013.01)

(58) Field of Classification Search
CPC ............. C07D 311/06; C07D 311/02

USPC ................... 549/289, 275; 526/266
See application file for complete search history.

(56) References Cited

U.S. PATENT DOCUMENTS

| | | | |
|---|---|---|---|
| 4,347,350 | A | 8/1982 | Horner |
| 5,925,498 | A | 7/1999 | Dominh |
| 2002/0173616 | A1 | 11/2002 | Matsuda |
| 2004/0019132 | A1 | 1/2004 | Long |
| 2005/0175708 | A1 | 8/2005 | Carrasquillo |
| 2011/0318772 | A1 | 12/2011 | Diwu |

FOREIGN PATENT DOCUMENTS

| | | |
|---|---|---|
| CN | 102153856 A | 8/2011 |
| EP | 0 453 237 B1 | 12/1998 |

OTHER PUBLICATIONS

Shibu, E.S. et al.: Photouncaging Nanoparticles for MRI and Fluorescence imaging in vitro and in vivo. ACS Nano, vol. 7, pp. 9851-9859, 2013.*

Leenders et al. Photochemistry of Nonconjugated Bichromophoric Systems, Cyclomerization of 7,7'-Polymethylenedioxycoumarins and Polymethylenedicarboxylic Acid (7-Coumarinyl) Diesters. J. Org. Chem., 38(5):957-966, 1973. entire document.

Han et al. Biodegradable Cell-Seeded Nanofiber Scaffolds for Neural Repair. Polymers, 3(4): 1684-1773, 2011. [retrieved on Feb. 21, 2014]. Retrieved from the Internet: <URL:http://www.mdpi.com/2073-4360/3/4/1684>. entire document.

He et al. Light-responsive polymer micelles, nano- and microgels based on the reversible photodimerization of coumarin. Dyes and Pigments, 89(3):278-283, 2011. entire document.

Fu, et al.; Preparation and reversible phot-crosslinking/photo-cleavage behaviour of 4-methylcoumarin functionalized hyperbranched polyester: Polymer 29 (2008) 4981-4988.

Chen, et al.; Synthesis and Reversible Photocleavage of Novel Polyurethanes Containing Coumarin Dimer Components: journal of Polymer Science Part A; Polymer Chemistry, vol. 35, 613-624 (1997).

* cited by examiner

*Primary Examiner* — Charanjit Aulakh
(74) *Attorney, Agent, or Firm* — Renner Kenner Greive Bobak Taylor & Weber (57) ABSTRACT

A photoactive coumarin monomer includes a substituted coumarin molecule that has at least two functional groups may be used to produce a polymer with a coumarin unit or a coumarin derivative unit as part of the polymer backbone. The polymer with a coumarin unit or a coumarin derivative unit as part of the polymer backbone may be photoresponsive and/or bioabsorbable. Photoresponsive polymers with a coumarin unit or a coumarin derivative unit as part of the polymer backbone may crosslink when irradiated at a wavelength of about 320 nm to about 420 nm. The crosslink may be separated when the polymers are irradiated at a wavelength of about 230 nm to about 300. The polymers may also photocleave when irradiated with light at a wavelength of about 230 nm to about 300.

9 Claims, 5 Drawing Sheets

PHOTORESPONSIVE COUMARIN BASED POLYMERS: SYNTHESIS AND APPLICATIONS

CROSS-REFERENCE TO RELATED APPLICATIONS

This application claims priority from U.S. Provisional Patent Application No. 61/723,849 filed on Nov. 8, 2012, the contents of which are incorporated herein by reference.

FIELD OF THE INVENTION

One or more embodiments provides photoresponsive coumarin based polymers, methods of using photoresponsive coumarin based polymers, methods of preparing photoresponsive coumarin based polymers, and photoactive coumarin monomers that may be used in one or more embodiments to produce photoresponsive coumarin based polymers.

BACKGROUND OF THE INVENTION

Materials designed to be responsive to light have several advantages as it involves spatiotemporal control of the polymer in precise and robust manner. Of late, polymers which exhibit both photo- and biodegradable properties have become increasingly desirable. Polymers with such properties could be activated by the photochemical input and at a later stage undergo hydrolysis either in the aqueous biological environment or in the nature. Such polymers display numerous applications in environmental, agricultural and biomedical fields.

Coumarin groups have previously been used in synthetic organic chemistry as a tool for orthogonal deprotection. Other uses for coumarin groups include uncaging molecules such as neurotransmitters, as labile groups in solid phase peptide synthesis, for formation of functionalized channels in agarose hydrogels, and in photodegradable scaffolds for tissue engineering. However, the prior art does not include coumarin groups that are part of a polymer chain, where they are advantageously part of a polymer that may be photoresponsive and/or bioabsorbable.

SUMMARY OF THE INVENTION

A first embodiment provides a polymer comprising a polyurethane or a polyester with a coumarin unit or a coumarin derivative unit as part of the polymer backbone.

A second embodiment provides a polymer as in the first embodiment, where the coumarin unit or a coumarin derivative unit defined by the formula:

where each $R^2$ is individually a hydrogen atom, a bromine atom, an iodine atom, or a methoxy group; $R^3$ is a hydrocarbon group; $R^4$ is a hydrocarbon group; Y is an oxygen atom or a nitrogen atom with an organic substitution; Z is selected from ester groups or urethane groups; and $\alpha$ is an oxygen atom or a sulfur atom.

A third embodiment provides a polymer as in the either the first or second embodiment, where the coumarin unit or the coumarin derivative unit is defined by the formula:

A forth embodiment provides a polymer as in any of the first through third embodiments, where the coumarin unit or the coumarin derivative unit is crosslinked to a second coumarin unit or coumarin derivative unit.

A fifth embodiment provides a polymer as in any of the first through forth embodiments, where the crosslink is defined as:

where each $R^2$ is individually a hydrogen atom, a bromine atom, an iodine atom, or a methoxy group; each $R^3$ is independently a hydrocarbon group; each $R^4$ is independently a hydrocarbon group; each Y is independently an oxygen atom or a nitrogen atom with an organic substitution; each Z is independently selected from ester groups or urethane groups; and each $\alpha$ is independently an oxygen atom or a sulfur atom.

A sixth embodiment provides a bone graft substitute comprising a calcium hydroxyphosphate; and the polymer as in any of the first through fifth embodiments.

A seventh embodiment provides a method of preparing a polymer comprising: reacting a diisocyanate or a dicarboxylic acid with a photoreactive coumarin monomer defined by the formula:

where each $R^2$ is individually a hydrogen atom, a bromine atom, an iodine atom, or a methoxy group; $R^3$ is a hydrocarbon group; Y is an oxygen atom or a nitrogen atom with an organic substitution; and α is an oxygen atom or a sulfur atom.

An eighth embodiment provides a method of preparing a polymer as in the seventh embodiment, where the alkoxyalkoxy-coumarin derivative is reacted with a diisocyante defined by the formula where R4 is a hydrocarbon group.

A ninth embodiment provides a method of preparing a polymer as in the either the seventh or eight embodiment, where the diisocyante is selected from the group consisting of hexamethylene diisocyanate and 1,3-phenylene diisocyanate A tenth embodiment provides a method of preparing a polymer as in any of the seventh through ninth embodiments, where the alkoxyalkoxy-coumarin derivative is reacted with a dicarboxylic acid defined by the formula where $R^4$ is a hydrocarbon group.

An eleventh embodiment provides a method of preparing a polymer as in any of the seventh through tenth embodiments, where the dicarboxylic acid is selected from the group consisting of succinic acid, glutaric acid, adipic acid, pimelic acid, suberic acid, sebacic acid, protected glutamic acids, protected aspartic acids, terepthalic acid, pthalic acid and isopthalic acid.

A twelfth embodiment provides a method of crosslinking polymers comprising irradiating the polymers prepared as in any of the seventh through eleventh embodiments.

A thirteenth embodiment provides a method of preparing a patterned surface comprising; irradiating a polyurethane or a polyester polymer film with a coumarin unit or a coumarin derivative unit as part of the polymer backbone with a wavelength of light of about 320 nm to about 420 nm, about 230 nm to about 300, or a combination thereof.

A fourteenth embodiment provides a method of preparing a nerve guidance device comprising: preparing a patterned surface by irradiating a polyurethane or a polyester polymer film with a coumarin unit or a coumarin derivative unit as part of the polymer backbone in the polymer film with a wavelength of light of about 320 nm to about 420 nm, about 230 nm to about 300, or a combination thereof to create a cavity or channel in the film; and seeding nervous system cells within the cavity or channel in the film.

A fifteenth embodiment provides a method of preparing a nerve guidance device as in the fourteenth embodiment, where the nerve guidance device is a nerve guidance conduit.

A sixteenth embodiment provides a composition for the controlled release of a small molecule comprising a small molecule encapsulated by a polymer matrix of a polyurethane or a polyester, wherein the a polyurethane or a polyester includes a coumarin unit or a coumarin derivative unit.

A seventeenth embodiment provides a composition for the controlled release of a small molecule as in the sixteenth embodiment, where the polymer with a polyurethane or a polyester with a coumarin unit or a coumarin derivative unit is defined by the formula:

where each R2 is individually a hydrogen atom, a bromine atom, an iodine atom, or a methoxy group; each R3 is independently a hydrocarbon group; each R4 is independently a hydrocarbon group; each Y is independently an oxygen atom or a nitrogen atom with an organic substitution; each Z is independently selected from ester groups or urethane groups; and each α is independently an oxygen atom or a sulfur atom.

An eighteenth embodiment provides a composition for the controlled release of a small molecule as in either the sixteenth or seventeenth embodiments, where the small molecule is selected from drugs; peptides; and enhancers and additives used in cosmetics, fragrances, pesticides, agricultural fertilizers; and combination there of.

A nineteenth embodiment provides a method for the controlled release of a small molecule comprising; irradiating the composition of claim 16 with light at a wavelength of irradiated at a wavelength of about 320 nm to about 420 nm, about 230 nm to about 300, or a combination thereof.

A twentieth embodiment provides a photoactive coumarin monomer defined by the formula:

where each $R^1$ is individually an alcohol, a carboxylic acid, an isocyanate, or a primary amine group; each $R^2$ is individually a hydrogen atom, a bromine atom, an iodine atom, or a methoxy group; $R^3$ is a hydrocarbon group; Y is an oxygen atom or a nitrogen atom with an organic substitution; and α is an oxygen atom or a sulfur atom.

A twenty-first embodiment provides a photoactive coumarin monomer as in the first twentieth embodiment, where the monomer is defined by the formula:

DETAILED DESCRIPTION OF ILLUSTRATIVE EMBODIMENTS

In one or more embodiments, the present invention provides a photoactive coumarin monomer comprising a substituted coumarin molecule that includes at least two functional groups. In one or more embodiments, the photoactive coumarin monomer may be used to produce a polymer with a coumarin unit or a coumarin derivative unit as part of the polymer backbone. In these or other embodiments, the photoactive coumarin monomer includes at least two functional groups capable of reacting to provide a coumarin unit or a coumarin derivative unit as part of the polymer backbone. Those skilled in the art will appreciate that a coumarin molecule may be defined by the following formula:

Derivatives of the photoactive coumarin monomer may include substitutions at either oxygen atom of the base coumarin molecule. In one or more embodiments, the photoactive coumarin monomer may have a sulfur atom substituted for the oxygen atom on the carbonyl carbon of the base coumarin molecule. In these or other embodiments, the photoactive coumarin monomer may have a nitrogen atom substituted for the oxygen atom. In these or other embodiments, the photoactive coumarin monomer may have organic groups substituted at any of the hydrogen atoms of the base coumarin molecule.

Photoactive coumarin monomers are useful in the production of polymers because they can be used to provide a reversible crosslink. Polymers prepared with photoactive coumarin monomers include a coumarin unit or a coumarin derivative unit capable of undergoing photodimerization with another coumarin unit or a coumarin derivative unit when the polymer is irradiated with light. In one or more embodiments, polymers with a coumarin unit or a coumarin derivative unit undergo photodimerization when irradiated at a wavelength of about 320 nm to about 420 nm. The dimerization may be reversed by the irradiation of a cross-linked polymer. In one or more embodiments, the dimer of coumarin units or coumarin derivative units may separate when irradiated at a wavelength of about 230 nm to about 300 nm.

In one or more embodiments, the photoreactive coumarin monomer defined by the formula:

where each $R^1$ is individually an alcohol, a carboxylic acid, an isocyanate, or a primary amine group; each $R^2$ is individually a hydrogen atom, a bromine atom, an iodine atom, or a methoxy group; $R^3$ is a hydrocarbon group; Y is an oxygen atom or a nitrogen atom with an organic substitution; and α is an oxygen atom or a sulfur atom.

In one or more embodiments, the photoreactive coumarin monomer defined by the formula:

where each $R^2$ is individually a hydrogen atom, a bromine atom, an iodine atom, or a methoxy group; $R^3$ is a hydrocarbon group; Y is an oxygen atom or a nitrogen atom with an organic substitution; and α is an oxygen atom or a sulfur atom.

Suitable organic substitutions for the nitrogen atoms with an organic substitution include, but are not limited to, methyl, ethyl, and phenyl groups.

Suitable hydrocarbon groups capable of being an $R^3$ group include linear, cyclic, or branched hydrocarbon groups. In one or more embodiments, the $R^3$ is a hydrocarbon group of from 2 to 8 carbons, in other embodiments, from 2 to 6 carbons, and in yet other embodiments, from 2 to 4 carbons.

Specific examples of photoactive coumarin monomers include those defined by the following structures:

and

In one or more embodiments, a polymer may be prepared by reacting a diisocyanate or a dicarboxylic acid with a photoactive coumarin monomer. In one or more embodiments, the amount of the diisocyanate or dicarboxylic acid employed can be described with reference to the photoactive coumarin monomer. For example, the molar ratio of the diisocyanate or dicarboxylic acid to the photoactive coumarin monomer may be from about 0.1:1 to about 9:1, in other embodiments from about 1:1 to about 4:1, and in other embodiments from about 2:1 to about 3:1.

In one or more embodiments, where a dicarboxylic acid is reacted with a coumarin monomer, a polyester with a coumarin unit or a coumarin derivative unit may be formed. In one or more embodiments, a polyester with a coumarin unit or a coumarin derivative unit may be formed by reacting a dicarboxylic acid and a coumarin monomer with a polyesterification catalyst such as 4-(N,N dimethylamino) pyridinium-4-toluenesulfonate catalyst in dichloromethane and N,N-diisopropylcarbodiimide. The polyester with a coumarin unit or a coumarin derivative unit may be precipitated with alcohols.

In one or more embodiments, where a diisocyanate is reacted with a coumarin monomer, a polyurethane with a coumarin unit or a coumarin derivative unit may be formed. In one or more embodiments, a polyurethane with a coumarin unit or a coumarin derivative unit may be formed by reacting a diisocyanate and a coumarin monomer with a step growth polymerization catalyst such as Sn(II)octoate catalyst in N,N-dimethylformamide. The polyurethane with a coumarin unit or a coumarin derivative unit may be precipitated with alcohols.

In one or more embodiments, the diisocyante may be defined by the formula:

where $R^4$ is a hydrocarbon group. Suitable hydrocarbon groups capable of being an $R^4$ group include linear hydrocarbon, cyclic hydrocarbon, branched hydrocarbon groups, or aromatic groups. In one or more embodiments, the $R^4$ group is a hydrocarbon group from 6 to 10 carbon atoms, in other embodiments, from 6 to 8 carbon atoms, and in yet other embodiments about 6 carbons.

Suitable diisocyante compounds include but are not limited to, those selected from the group consisting of hexamethylene diisocyanate and 1,3-phenylene diisocyanate.

In one or more embodiments, the dicarboxylic acid may be defined by the formula:

where $R^4$ is a hydrocarbon group. Suitable hydrocarbon groups capable of being an $R^4$ group include linear, cyclic, branched hydrocarbon groups or aromatic groups. In one or more embodiments, the $R^4$ group is a hydrocarbon group of from 2 to 8 carbon atoms, in other embodiments, from 2 to 6 carbon atoms, and in yet other embodiments from 2 to 4 carbons.

Suitable dicarboxylic acid compounds include, but are not limited to, those selected from the group consisting of succinic acid, glutaric acid, adipic acid, pimelic acid, suberic acid, sebacic acid, protected glutamic acids, such as Boc-Glu-OH, protected aspartic acids, such as Boc-Asp-OH, terepthalic acid, pthalic acid and isopthalic acid.

In one or more embodiments, a diol comonomer and the photoactive coumarin monomer may be reacted with a diisocyanate or a dicarboxylic acid to produce a polymer. In one or more embodiments, the amount of the diol comonomer employed can be described with reference to the photoactive coumarin monomer. For example, the molar ratio of the diol comonomer acid to the photoactive coumarin monomer may be from about 0.1:1 to about 10:1, in other embodiments from about 0.5:1 to about 5:1, and in other embodiments from about 1:1 to about 3:1.

In one or more embodiments, the diol comonomer may be defined by the formula:

where $R^5$ is a hydrocarbon group. Suitable hydrocarbon groups capable of being an $R^5$ group include linear, cyclic, branched hydrocarbon groups, aromatic groups, or polyhydrocarbyl glycols. These groups may be substituted at a carbon atom with a hetero atom. Examples of heteroatoms include oxygen, sulfur and nitrogen. In one or more embodiments, the $R^5$ group is a hydrocarbon group from 2 to 10 carbon atoms, in other embodiments, from 6 to 8 carbon atoms, and in yet other embodiments about 6 carbons.

Suitable diol comonomer compounds include, but are not limited to, polyethylene glycol diols (PEG diols) with a molecular weight from 200 to 8,000 g/mol, diols, polycaprolactone diols (PCL-diols) with a molecular weight from 500 to 5000 g/mol, and bis(hydroxyethyl)hydroquinone. Specific examples of PEG diols include PEG 400, PEG 1000, PEG 2000, and PEG 5000.

As previously noted, a polymer produced from a photoactive coumarin monomer may include a coumarin unit or a coumarin derivative unit as part of the polymer backbone. In one or more embodiments, a polyurethane or a polyester with a coumarin unit or a coumarin derivative unit as part of the polymer backbone may be prepared. In these or other embodiments, the a polymer with a coumarin unit or a coumarin derivative unit defined by the formula:

where each $R^2$ is individually a hydrogen atom, a bromine atom, an iodine atom, or a methoxy group; $R^3$ is a hydrocarbon group; $R^4$ is a hydrocarbon group; Y is an oxygen atom or a nitrogen atom with an organic substitution; Z is selected from ester groups or urethane groups; and α is an oxygen atom or a sulfur atom. The use of the symbol " ⁓ " denotes a polymer chain.

In these or other embodiments, the a polymer with a coumarin unit or a coumarin derivative unit defined by the formula:

In one or more embodiments, a polymer with a coumarin unit or a coumarin derivative unit defined by the formula:

where n is about 5 to 25 units; p is about 5 to 200 units; each $R^2$ is independently a hydrogen or an organic group; $R^3$ is a hydrocarbon group; each $R^4$ is independently a hydrocarbon group; each $R^5$ is independently a hydrocarbon group; W is selected from $$\underset{H}{\overset{O}{\|}}\text{—C—N—} \quad \text{and} \quad \overset{O}{\overset{\|}{\text{—C—}}};$$

Y is an oxygen atom or a nitrogen atom with an organic substitution; each Z is independently selected from ester groups or urethane groups; and a is an oxygen atom or a sulfur atom.

In one or more embodiments, a polymer with a coumarin unit or a coumarin derivative unit defined by the formula:

where n is about 5 to 25 units; p is about 5 to 200 units; each $R^4$ is independently a hydrocarbon group; each $R^5$ is independently a hydrocarbon group; each Z is independently selected from ester groups or urethane groups.

As previously noted, a polymer containing a coumarin unit or a coumarin derivative unit may be crosslinked by irradiating the polymers with light. In these or other embodiments, a coumarin unit or the coumarin derivative unit is crosslinked to a second coumarin unit or coumarin derivative unit. The crosslinking forms dimers where two coumarin units or the coumarin derivative units are connected through a cyclobutane group.

The amount of dimerization of the coumarin units or the coumarin derivative units may be controlled by varying the intensity, duration, and wavelength of the irradiated light. For example, if additional crosslinking is desired the exposure time of irradiation at a wavelength of about 320 nm to about 420 nm may be increased. Conversely, if less crosslinking is desired exposure time of irradiation at a wavelength of about 230 nm to about 300 nm may be increased.

In one or more embodiments, a dimer formed from two coumarin units or coumarin derivative units may produce a polymer with a crosslink defined as:

where each R2 is individually a hydrogen atom, a bromine atom, an iodine atom, or a methoxy group; each $R^3$ is independently a hydrocarbon group; each $R^4$ is independently a hydrocarbon group; each Y is independently an oxygen atom or a nitrogen atom with an organic substitution; each Z is independently selected from ester groups or urethane groups; and each α is independently an oxygen atom or a sulfur atom. Although shown as a head-to-tail structure, the above structure is intended to represent both syn- and anti-conformations of the head-to-head and head-to-tail dimers.

In one or more embodiments, the polymer may undergo photo cleavage. In these or other embodiments, the polymer containing a coumarin unit or a coumarin derivative unit may undergo photocleavage at about 230 to 300 nm. In one or more embodiments, photocleavage on the polymer containing a coumarin unit or a coumarin derivative may take place on the structure below at the bond locations indicated with dotted lines.

where each $R^2$ is a hydrogen or an organic group; $R^3$ is a hydrocarbon group; $R^4$ is a hydrocarbon group; Y is an oxygen atom or a protected nitrogen atom; Z is selected from ester groups or urethane groups; and α is an oxygen atom or a sulfur atom.

In one or more embodiments, the polymer containing a coumarin unit or a coumarin derivative unit may be characterized by the polymer's molecular weight in the uncrosslinked form. In one or more embodiments, the polymer containing a coumarin unit or a coumarin derivative unit is characterized by a molecular weight that is at least 8000, in other embodiments at least 20,000, and in other embodiments at least 40,000. In these or other embodiments, the polymer containing a coumarin unit or a coumarin derivative unit is characterized by a molecular weight that is at most 60,000, in other embodiments at most 80,000, and in other embodiments at most 160,000. In certain embodiments the polymer containing a coumarin unit or a coumarin derivative unit may be characterized by a molecular weight that is from about 8,000 to about 160,000, in other embodiments from about 20,000 to about 80,000, and in other embodiments from about 40,000 to about 60,000.

In one or more embodiments, the polymer containing a coumarin unit or a coumarin derivative unit may be characterized by the average number of coumarin units or a coumarin derivative units within a polymer chain. In one or more embodiments, the polymer containing a coumarin unit or a coumarin derivative unit is characterized by an average number of coumarin units or a coumarin derivative units within a polymer chain that is at least 20, in other embodiments at least 50, and in other embodiments at least 70. In these or other embodiments, the polymer containing a coumarin unit or a coumarin derivative unit is characterized by an average number of coumarin units or a coumarin derivative units within a polymer chain that is at most 120, in other embodiments at most 150, and in other embodiments at most 250. In certain embodiments the polymer containing a coumarin unit or a coumarin derivative unit may be characterized by an average number of coumarin units or a coumarin derivative units within a polymer chain that is from about 20 to about 250, in other embodiments from about 50 to about 150, and in other embodiments from about 70 to about 250.

Advantageously, the polymer containing a coumarin unit or a coumarin derivative unit is soluble in a wide range of common organic solvents. The ability of the polymers containing a coumarin unit or a coumarin derivative unit soluble in a wide range of common organic solvents allows for the polymers to be handled and processed easily. Suitable solvents for dissolving polymers containing a coumarin unit or a coumarin derivative unit include, but are not limited to, dichloromethane, chloroform, dimethylformamide, and dimethyl sulfoxide.

In one or more embodiments, a bone graft substitute may be prepared from a polymer containing a coumarin unit or a coumarin derivative unit. Polymers containing a coumarin unit or a coumarin derivative unit are particularly suited for use in bone grafts because of the polymer's photo crosslinking properties and the polymer's ability to biodegrade. The bone graft substitute may be used in a surgery to replace portions of bone. Advantageously, a bonegraft substitute may be prepared that will flow or be malleable. Then once positioned, the bone graft substitute may be irradiated to crosslink the polymers, thus hardening the bone graft in the desired conformation. In one or more embodiments, the bone graft substitute may include a calcium hydroxyphosphate ($Ca_5(OH)(PO_4)_3$ (hydroxyapatite), and a polyurethane or a polyester polymer with a coumarin unit or a coumarin derivative unit as part of the polymer backbone.

In one or more embodiments, a composite may be prepared by blending a coumarin unit or a coumarin derivative unit with silicate particles.

In one or more embodiments, a patterned surface may be prepared from a polymer containing a coumarin unit or a coumarin derivative unit. The pattern may be a cavity or a channel embedded in the surface. In one or more embodiments, the width of the pattern may be on the microscale. The microscale includes patterns with cavity or a channel with a width of 2 µm to 100 µm. The depth of the channel or cavity or a channel may be up to 20 µm.

In one or more embodiments, a patterned surface may be prepared by irradiating a polyurethane or a polyester polymer film with a coumarin unit or a coumarin derivative unit as part of the polymer backbone.

In one or more embodiments, a polyurethane or a polyester polymer film is a thin sheet of polyurethane or polyester. In one or more embodiments, a film may contain other components drugs, antibiotics and dyes In one or more embodiments, the polymer film may be about 10 nm to about 200 nm thick, in other embodiments, about 100 nm to about 120 nm thick, and in still other embodiments about 150 nm to 200 nm thick. A film may be prepared by dissolving the polymer in a solvent and dispersing the polymer, for example by spin coating the polymer onto a substrate.

Due to the ability of polymers containing a coumarin unit or a coumarin derivative unit to photocrosslink and photocleave, patterned surfaces may be created in multiple ways. In one or more embodiments, a patterned surface may be created by placing a masking pattern on or over a polymer film to cover areas where a channel or cavity is desired. The film may then be irradiated with light at a wavelength of about 350 nm to crosslink the polymer surface exposed to the light. The masked sections, or polymer to be removed, may then be removed to yield a patterned surface. In other embodiments, a patterned surface may be created by placing a masking pattern on or over a polymer film to cover areas where a channel or cavity is not desired. The film may then be irradiated with light at a wavelength of about 254 nm to photocleave the polymer surface exposed to the light. The unmasked sections, or polymer to be removed, may then be removed to yield a patterned surface. In one or more embodiments, the polymer to be removed may be washed away with suitable solvents. Non limiting examples of suitable solvents include chloroform, methanol, and combinations thereof.

In one or more embodiments, electronic patterns may be prepared. Electronic patterns may be prepared with specific dimensions using a vector program. The electronic patterns may be focused on to the polymer without a mask and light. For example, electronic patterns were prepared (Ridge X Channel: 10 µm×30 µm or 10 µm×60 µm) by Inkscape, an open source vector graphics editor program. The electronic patterns were focused on to the polymer-coated cover slips without a mask and exposed to 365 nm (UV) (USHIO (Discharge) Super High Pressure Mercury lamps, USH-350D) for 15 minutes.

Other methods to make such patterned surfaces would be use lower power light sources such as commercially available instruments like a Rayonet reactor, or a Dymax light source or higher power sources such as lasers.

In one or more embodiments, a nerve guidance device may be prepared from a polymer containing a coumarin unit or a coumarin derivative unit. Polymers containing a coumarin unit or a coumarin derivative unit are particularly suited for use in nerve guidance devices because of the polymer's ability to make patterned surfaces and the polymer's ability to biodegrade.

In one or more embodiments, the nerve guidance device may be prepared by preparing a patterned surface by irradiating a polyurethane or a polyester polymer film with a coumarin unit or a coumarin derivative unit as part of the polymer backbone in the polymer film to create a cavity or channel in the film; and seeding neural cells within the cavity or channel in the film. The patterned surface may be used to guide the proliferation of the seeded cells. In one or more embodiments, the patterned surface has a plurality of channels and/or cavities.

Suitable cells for use in a nerve guidance device are nerve cells including but not limited to, as, cortical neurons, neural stem cells, and schwan cells etc.

Though noted as a nerve guidance device, other types of cells may also be guided by a patterned polyurethane or a polyester polymer film with a coumarin unit or a coumarin derivative unit as part of the polymer backbone. For example cardiomyocytes and endothelial cells.

In one or more embodiments, the nerve guidance device may be a nerve guidance conduit. A nerve guidance conduit may be prepared from a tubular polymer film with a patterned interior surface. Neural cells may be seeded in the interior of the nerve guidance conduit where the patterned inner surface may be used to guide the proliferation of the seeded cells. A nerve guidance conduit may be inserted in a patient through surgery to bridge nerve damage. Advantageously, using polyurethane or a polyester polymer film with a coumarin unit or a coumarin derivative unit as part of the polymer backbone provides a nerve guidance conduit that may be patterned easily through photocrossslinking and photocleaving, and is also bioabsorbable.

In one or more embodiments, a composition for the controlled release of small molecules may be prepared from a polymer containing a coumarin unit or a coumarin derivative unit. A composition for the controlled release of a small molecule may be prepared by encapsulating a small moleculein a polymer matrix of a polyurethane or a polyester, wherein the a polyurethane or a polyester includes a coumarin unit or a coumarin derivative unit. Polymers containing a coumarin unit or a coumarin derivative unit are particularly suited for use in compositions for the controlled release of a small molecules because of the polymer's photocrosslinking properties and the polymer's ability to biodegrade. Polymers containing a coumarin unit or a coumarin derivative unit may be used in controlled release composition in ocular, cosmetic, agricultural and coatings fields.

In one or more embodiments, a composition of the controlled release of a small molecule comprising a polymer with a polyurethane or a polyester with a coumarin unit or a coumarin derivative unit; and a small molecule. Suitable small molecules that may be used in controlled release compositions include, but are not limited to, drugs; peptides; and enhancers and additives used in cosmetics, fragrances, pesticides, agricultural fertilizers; and combination there of.

Advantageously, the ability of polymers containing a coumarin unit or a coumarin derivative unit to photo crosslink and photocleave allows for the controlled release composition to be controlled through the intensity, duration, and wavelength of light used. In one or more embodiments, the composition of the controlled release of a small molecules may be irradiated with light at a wavelength of about 230 nm to about 300 nm, about 320 nm to about 420 nm, or a combination thereof. For instance, if a slow controlled release is desire, the polymers containing a coumarin unit or a coumarin derivative unit in the composition of the controlled release of a small molecules may be irradiated with light at a wavelength of about 320 nm to about 420 nm to crosslink the polymers, thus slowing the rate of release of the small molecules. Conversely, the release of small molecules may be increased by irradiating the composition of the controlled release of a small molecules a wavelength of about 230 nm to about 300 nm to uncrosslink the polymers and, in some embodiments, photocleave the polymers, thus increasing the rate of release of the small molecules.

Devices of such polymers can be fabricated into nanoparticles, films, fibers, hydrogels etc., which may have controlled release applications in ocular, cosmetic, agricultural and coatings fields.

In order to demonstrate the practice of the present invention, the following examples have been prepared and tested. The examples should not, however, be viewed as limiting the scope of the invention. The claims will serve to define the invention.

Examples

Unless otherwise noted, solvents were purchased from Fisher Scientific and were used as received. Acetone was dried over activated 4 Å molecular sieves. Sodium bisulfate, potassium carbonate, 18-crown-6, p-toluenesulfonic acid, dichloromethane (extra dry), 4 Å molecular sieves, 3-bromo-1-propanol, and adipic acid were purchased from Acros Organics, ethyl 4-chloroacetoacetate and hydroquinone bis(2-hydroxyethyl) ether were purchased from Alfa Aesar, and diisopropylcarbodiimide (DIC) was purchased from Oakwood Chemicals and used without further purification.

NMR Spectroscopy. Solution: 1H NMR spectra were recorded on a Varian Mercury 300 MHz or Varian 500 MHz spectrometer. 13C NMR spectra were recorded at 125 MHz on a Varian 500 MHz spectrometer. Chemical shifts were recorded in ppm (δ) relative to TMS. Solid state: 13C CPMAS NMR spectra were obtained using BRUKER Avance III 300 NMR spectrometer equipped with a 4 mm double resonance CP/MAS NMR probe. The magic angle spinning (MAS) frequency was set to 12 000±5 Hz. The 1H 90° pulse length is 3.75 μs. High-power 1H TPPM decoupling with a field strength of 65 kHz is applied during signal acquisition. Cross-polarization (CP) contact time and recycle delay were 1.5 ms and 2 s, respectively. Chemical shift was calibrated using CH signal of adamantine at 29.46 ppm as an external reference. Each spectrum was obtained by 10 240 scans at ambient temperature. Gaussian peaks were applied for spectral fitting. The signal intensity obtained by CP method highly relies on CP efficiency.

GPC Analysis. GPC was performed on two TSK-GEL Super H 3000 columns and one TSK-GEL Super H 4000 column in series and analyzed using a TOSOH EcoSEC HLC-8320 instrument. Samples were dissolved in CHCl₃ with a constant flow rate of 0.4 mL/min. Molecular weights were obtained relative to PS standards. ATR-IR and UV Analysis. IR spectra of the free-standing solid films were recorded on a Shimadzu MIRacle 10 ATR-FTIR. UV was recorded on a Shimadzu UV-1800 UV spectrophotometer. AFM was obtained on DI MultiMode SPM AFM (Tapping mode). Tensile modulus was measured in the Applied Polymer Research Center at The University of Akron (Dynamic Mechanical Analysis). Specimens were cut into 14 mm long, 9.75 mm wide, and 0.06 mm thick samples. The samples were measured under uniaxial tension at 0.04 mm/s.

Fluorescence Microscopic Images. Polymers CA11 (4) and CAQ (5) were flow coated on precleaned microscopic glass slides and kept under vacuum for 24 h. Macroscopic template (1 cm×1 cm, 200 mM sized patterns) placed on top of the glass slides and irradiated at 254 nm (and 350 nm) wavelength light for 40 min. The irradiated samples were kept in CHCl₃/MeOH (30:70) for 30 min and then rinsed quickly in CHCl₃/MeOH (70:30) for 2-3 min. These glass slides were kept under vacuum for 24 h before taking the fluorescence images. The optical images were obtained by automated fluorescence microscope with an Olympus IX81 microscope (Olympus, Center Valley, Pa.) equipped with a computer-controlled translation stage (Prior Scientific, Rockland, Mass.) and Metamorph software. The images of the excited samples were obtained using DAPI (4',6-diamidino-2-phenylindole) filter.

Synthesis of Monomer and Polymers (FIG. 1). 1: To a stirring solution of resorcinol (10 g, 91 mmol, 1 equiv) and 4-chloromethyl acetoacetate (17 g, 103 mmol, 1.14 equiv) in toluene (150 mL) was added p-toluenesulfonic acid (3.6 g, 19 mmol, 0.21 equiv). The solution was connected to a Dean-Stark apparatus and heated to reflux at 110° C. for 45 min. The reaction mixture was concentrated and purified by column chromatography (EtOAC:CH₂Cl₂ 1:9) to yielded a white solid 1 (12 g, 65% yield). 2: To a stirring solution of water (350 mL) was added 7-hydroxy-4-(chloromethyl) coumarin (1, 2.95 g, 14 mmol). The reaction mixture was refluxed for 3 days, filtered while hot, and cooled to room temperature over 12 h to yield off-white needles (2). The product was filtered and connected to vacuum overnight (2.7 g, quantitative). The product was used further without purification. 3: To a stirring solution of anhydrous acetone (15 mL), 2 (1.0 g, 5.2 mmol, 1 equiv), potassium carbonate (2 g, 14.5 mmol, 2.8 equiv), and 3-bromo-1-propanol (1.5 g, 10.8 mmol, 2.1 equiv) was added 18-C-6 (0.7 g, 2.65 mmol, 0.5 equiv). The mixture was stirred for 5 min and then transferred into a microwave reactor (CEM, Discover). The reaction mixture was refluxed at 55° C. for 40 min (power: 20-30 mW) and filtered. The solvent was removed under reduced pressure to yield a light yellow solid. Purification by column chromatography (EtOAC:hexane 4:1) yielded a white solid (1.18 g, 91%) (3). CA11 (4). In a two-neck round-bottom flask, 3 (250 mg, 1 mmol, 1 equiv), adipic acid (146 mg, 1 mmol, 1 equiv), and 4-(N,Ndimethylamino) pyridinium-4-toluenesulfonate (DPTS, 117 mg, 0.4 mmol, 0.25 equiv) were taken. The flask was vacuum backfilled 3 times with N2. Dichloromethane (2.5 mL) was added while cooling the flask at 0° C. After 15 min, N,N-diisopropylcarbodiimide (DIC, 470 mL, 3 mmol, 3 equiv) was added, and the reaction was allowed to stir at room temperature for 48 h. The polymer was precipitated in mixture of alcohols (MeOH:EtOH:PrOH 1:1:1). The polymer was collected, centrifuged, and dried under vacuum to yield a white solid 4 (310 mg, 85%).

CAQ (5). In a two-neck round-bottom flask, 3 (62.5 mg, 0.25 mmol, 0.25 equiv), hydroquinone bis(2-hydroxyethyl) ether (149 mg, 0.75 mmol, 0.75 equiv), adipic acid (146 mg, 1 mmol, 1 equiv), and DPTS (117 mg, 0.4 mmol, 0.25 equiv) were taken. The flask was vacuum backfilled three times with N₂. Dichloromethane (2.5 mL) was added while cooling the flask at 0° C. After 15 min, DIC (470 mL, 3 mmol, 3 equiv) was added, and the reaction was allowed to stir at room temperature for 72 h. The polymer was precipitated in mixture of cold alcohols (MeOH:EtOH:PrOH 1:1:1). The polymer was collected, centrifuged, and dried under vacuum to yield a white solid 5 (252 mg, 88%).

Biocompatibility Studies. a. Cell Culture. Macrophage cells (RAW 264.7) were obtained from ATCC (Manassas, Va.). The cells were cultured in humidified incubations (37° C., 5% CO2) in complete growth media comprised of Dulbecco's Modified Eagle Medium (DMEM), 10% fetal bovine serum (FBS), and antibiotics (100 μg/mL streptomycin and 100 units/mL penicillin).

b. MTT Assay. Macrophage cells (RAW 264.7) were used for all biocompatibility studies. Briefly, 5×10⁴ cells were plated per well in a 96-well plate and allowed to recover overnight. The cells were exposed to varying concentrations of polymer (dissolved in DMSO and added to the medium) solutions for 24 h. The treatment solutions were aspirated, and the cells were washed with PBS (100 μL) before MTT dye was added and incubated at 37° C. for 4 h. Aspiration of the dye solution was followed by solubilizing the MTT dye in DMSO (100 μL) and glycine buffer (0.1 M, 15 μL). The absorbance of each well was immediately measured using a microplate reader (Spectramax-340PC, Bucher Biotec AG, Basel, Switzerland) at 570 nm. The absorbance values obtained were plotted as a percentage of untreated (control) cells.

c. Macrophage Activation Studies. Macrophage activation was assessed based on reactive oxygen species (ROS) production using the fluorescent probe 2,7-dichlorodihydrofluorescein diacetate (DCFHDA). RAW 264.7 cells were plated (5×10⁴ cells/well) in a black 96-well plate and allowed to recover overnight before being exposed to treatment solutions containing varying concentrations of the polymers (dissolved in DMSO and added to the medium) for 16 and 24 h. Cells treated with hydrogen peroxide (100 μM) were used as the positive control. Afterward, the treatment solutions were aspirated, and the cell monolayer was rinsed with PBS before DCFH-DA was added and incubated for 60 min (37° C.). The monolayer was again rinsed twice with PBS before the fluorescence intensity was measured (excitation 485 nm, emission 528 nm). Fluorescence intensity measurements were normalized per microgram of protein in each well. The protein content was assessed using the Pierce BCA Protein Assay Kit (Fisher Scientific, Pittsburgh, Pa.).

d. Biocompatibility after Polymer Irradiation. Cellular viability and macrophage activation were also assessed after the polymer (CA11) was irradiated with UV light (350 nm for 20 min and 254 nm for 30 min) Cellular viability was measured after incubation (37° C., 24 h) RAW cells with the polymer treatment solutions (dissolved in DMSO and added to the medium) using the MTT assay. The extent of macrophage activation was assessed by measuring the level of nitrite production using untreated cells as negative controls. Briefly, RAW 264.7 cells were plated (5×10⁴ cells/well) and allowed to recover overnight before receiving treatment solutions containing the irradiated CA11 samples. Afterward, the level of nitrite in the growth media was measured using the Griess reagent system (Cayman, Ann Arbor, Mich.). Lipopolysaccharide (LPS, Sigma-Aldrich, St. Louis, Mo.) was used as the positive control, and all data points were expressed as a percentage of LPS-treated cells.

Figure 1:
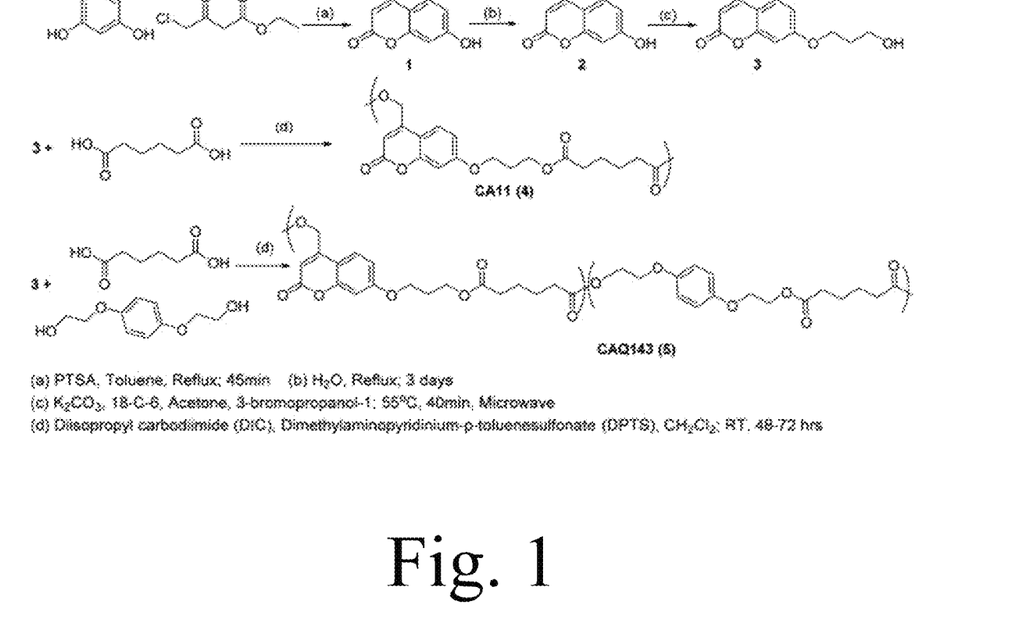
FIG. 1 provides a synthesis scheme of one or more embodiments of photoresponsive monomer and polymers FIG. 2 provides a scheme of the results of irradiation on or more embodiments of coumarin polyesters; irradiation at 350 nm leads to polymer chain cross-linking and irradiation at 254 nm leads to reverse un-cross-linking and/or ester cleavage reactions FIG. 3A provides an AFM image of the photomasked polymer surface after 350 nm irradiation of the photopatterns of the polymer CAQ.

The photoactive coumarin monomer 3 was synthesized as shown in FIG. 1. A published protocol was used to synthesize 7-hydroxy-4-(hydroxymethyl)coumarin (2). In order to facilitate polymer synthesis, 2 was chain extended to yield (7-(hydroxypropoxy)-4-(hydroxymethyl)coumarin (3) by microwave-assisted irradiation of 2 with 1-bromo-3-propanol and K2CO3 in 91% yields. Compared to published thermal methods of alkylation of phenols, this microwave-assisted alkylation reaction improved the yield for 3 from 25% to 91%. The diol (3) was subsequently reacted with adipic acid under carbodiimide/DPTS-catalyzed conditions to provide the homopolyester 4 (CA11). Similarly, a copolymer of the coumarin diol and the bis(hydroxyethyl)hydroquinone (5) (CAQ) was also synthesized and studied. Incorporation of a second diol in the polymer facilitates modulation of the mechanical properties and the efficiency of photoresponse of the polymers. These polymers were characterized by 1D/2D NMR, attenuated total reflectance IR (ATR-IR), and gel permeation chromatography (GPC). The polymers have UV absorption spectra from 250 to 370 nm with a λmax at 322 nm (molar extinction coefficient, $\epsilon = 7.1 \times 10^3$ M$^{-1}$ cm$^{-1}$). They possess high thermal stability ($T_d < 335\text{-}365°$ C.) and low glass transition temperatures ($T_g < 5\text{-}35°$ C., Table 1).

Figure 2:
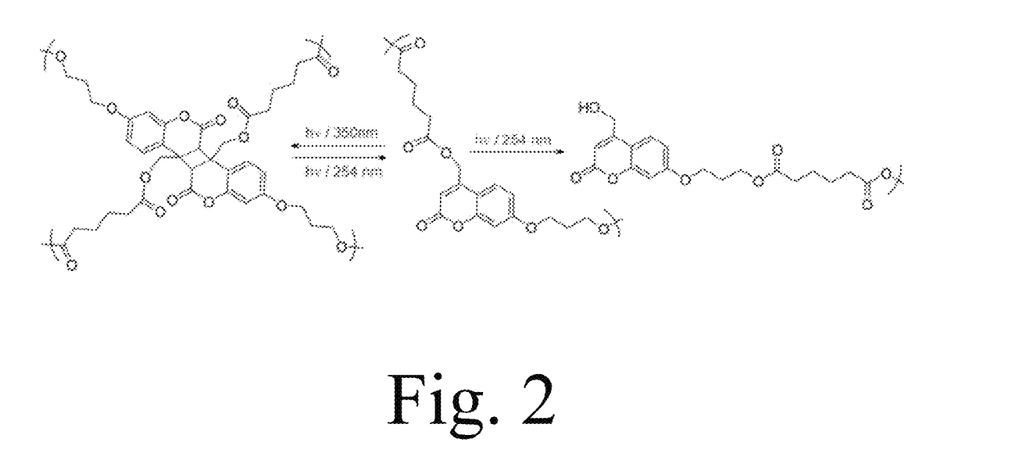

Irradiation of CA11 at 254 nm (2 mg/mL; CHCl3:MeOH 99:1; Rayonet reactor; 14 mW/cm² for 8 lamps, degassed with argon for 10 min; caution: irradiation of CHCl3 without degassing can generate toxic phosgene) leads to polymer chain scission by cleavage of the ester group at the fourth position on coumarin (FIG. 2), and gel permeation chromatography (GPC) analysis showed that within 40 min of irradiation the Mn of the homopolymer CA11 decreases from 21K to 4K. Alternatively, irradiation of the homopolymer CA11 at 350 nm (22 mW/cm², 16 lamps) leads primarily to polymer crosslinking (<82%). The area under the GPC curve reflects the total concentration of soluble sample; decreasing area under the curve therefore is an indirect measure of sample loss through the formation of insoluble cross-linked chains. The copolymer CAQ that contains a lower mol % of coumarin than the homopolymer CA11 upon irradiation at 254 nm for 40 min resulted in a decrease of molecular weight from 80K to 6K. Irradiation of polymer CAQ at 350 nm resulted in polymer cross-linking, and from the area under the peaks, it was estimated that 42% of the chains undergo crosslinking and become insoluble material. The difference in cross-linking efficiency can largely be attributed to the amounts of coumarin in polymer CA11 (50 mol %) and polymer CAQ (12.5 mol %), although the large difference in Mn between CA11 and CAQ may have an effect of polymer chain dynamics, which in turn may affect the photoresponse. At 350 nm the coumarin polyesters predominantly display a crosslinking reaction, which is also seen in coumarin-based small molecules and polymers. In the current coumarin polyesters CA11 and CAQ, irradiation at 350 nm also results in polymer chain scission due to photorelease of the ester substituent. However, contrary to small molecule phototriggers, polymer chain scission at 350 nm is the minor reaction. We attribute this difference to a higher local concentration of coumarin in our polymers when compared to the low concentrations of reported phototriggers.

Higher efficiency of polymer chain scission is observed at 254 nm, and this observation is analogous to work showing higher release efficiency of phenylalanine ester in coumarins and quinolones at 254 nm compared to 350 nm. These photocleavage and photo-cross-linking reactions at two different wavelengths were also monitored by UV-vis spectroscopy. Chain scission due to 254 nm irradiation does not change the overall chromophore structure in either CA11 or CAQ, so the UV spectra do not change. However, cross-linking at 350 nm leads to decrease in the coumarinyl band (322 nm).

To examine the details of photo-cross-linking and test the reversibility of the cross-linked polymer, solvent-cast films (thickness <70 μm) of polymer CA11 were irradiated at 350 nm and followed by attenuated total reflectance IR (ATR-IR) and solid-state 13C NMR (ssNMR). Irradiation at 350 nm results in cross-linking as indicated by the appearance of a new peak at 44 ppm, which corresponds to the resonance for the cyclobutane ring. Additionally, cross-linking decreases the intensity of the signal at 149 ppm, which corresponds to the C—C double bond of the coumarin. On the other hand, irradiation of the cross-linked polymer (CA11) film at 254 nm initiates the reverse reaction, as indicated by a decrease of the peak intensity at 44 ppm and increase of the peak at 149 ppm. Approximately 34% of the polymer was cross-linked upon irradiation at 350 nm for 5 min and 18% of it un-cross-linked after irradiation at 254 nm. These reactions can also be followed by ATR-IR which showed the disappearance and reappearance of C=C stretching frequency (1620 cm−1) at the expense of cyclic —C—C— bending frequency (1508 cm−1).

There is a need for materials that demonstrate variable modulus33 under specific stimuli, and these coumarin polyesters may have potential for such applications. Therefore, this aspect was examined by cross-linking the polymers by irradiation at 350 nm. As determined from tensile tests, the homopolymer CA11 has a Young's modulus of 68 MPa, and after irradiation at 350 nm, the modulus increases to 302 MPa. Similarly, the Young's modulus of the copolymer CAQ increased from 132 to 413 MPa (Table 1) after cross-linking.

TABLE 1

Physical Properties of the Polymers CA11 and CAQ

| polymer | $M_n{}^a$ (g/mol) | $PDI^a$ | $T_d$ (° C.) | $T_g$ (° C.) | % cross-linking$^a$ 254 nm$^c$ | % cross-linking$^a$ 350 nm$^c$ | modulus, $E^b$ (MPa) before hv$^d$ | modulus, $E^b$ (MPa) after hv$^e$ |
|---|---|---|---|---|---|---|---|---|
| CA11 (4) | 20 800 | 1.9 | 335 | 34-36 | 12 | 80 | 68 | 302 |
| CAQ143 (5) | 79 400 | 2.4 | 365 | 6-8 | 4 | 42 | 132 | 413 |

$^a$GPC analysis.
$^b$Measured by uniaxial tension.
$^c$Upon irradiation for 40 min.
$^d$Tensile modulus of the polymer measured before irradiation.
$^e$Tensile modulus of the polymer measured after irradiation at 350 nm for 40 min.

Micropatterned surfaces and devices have the potential to be useful for peripheral nerve guidance devices and for the investigation of cell-cell and cell-material interactions. Photoresponsive polymers that are also biodegradable, such as the ones described here, may be useful to fabricate guidance conduits that resorb after nerve regrowth, although more work needs to be carried out to show that this is the case. The dual photochemical behavior of these coumarin-based polymers enables the fabrication of complementary micropatterned surfaces from these materials. Polymer CA11 was coated onto a silicon wafer (<100-150 nm thickness) and irradiated either at 350 or 254 nm through a 1000 mesh TEM grid for 40 min and washed thoroughly with a CHCl$_3$/MeOH solvent mixture.

Figure 3A:
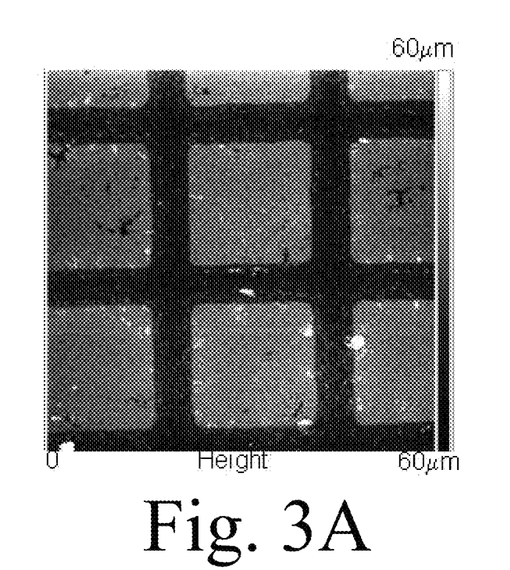
Figure 3B:
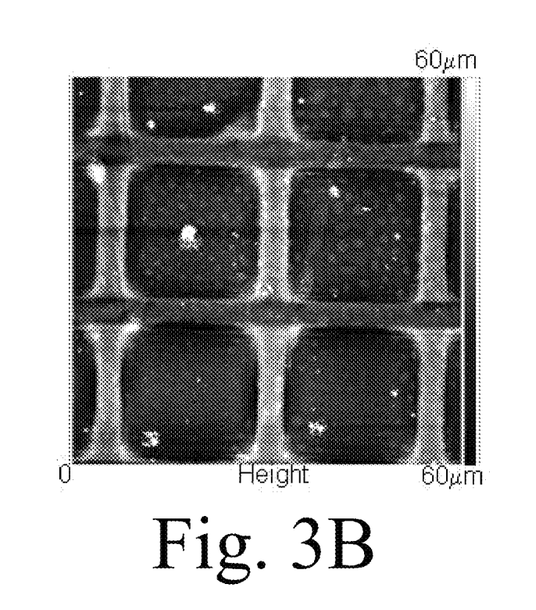
FIG. 3B provides an AFM image of the photomasked polymer surface after 254 nm irradiation of the photopatterns of the polymer CAQ.
Figure 3C:
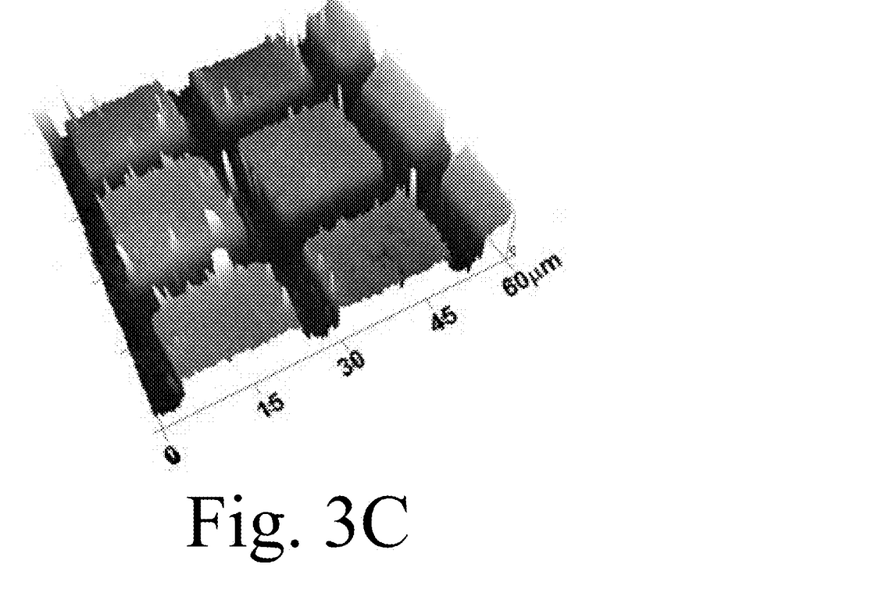
FIG. 3C provides an AFM image of the photomasked polymer surface after 350 nm irradiation of the photopatterns of the polymer CAQ.
Figure 3D:
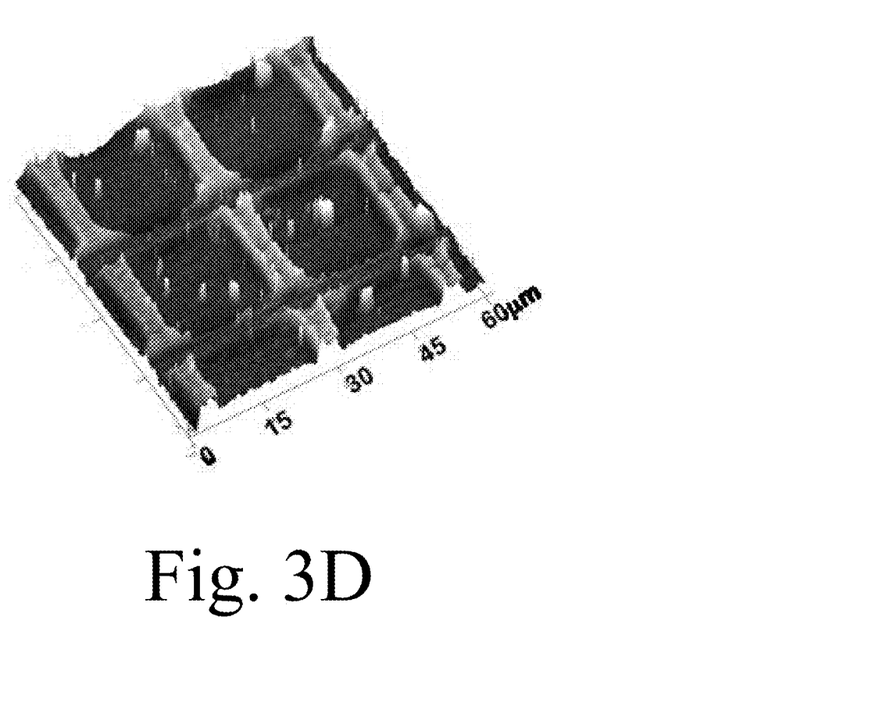
FIG. 3D provides an AFM image of the photomasked polymer surface after 254 nm irradiation of the photopatterns of the polymer CAQ.

As shown in FIG. 4, complementary TEM grid patterns are obtained by 350 and 254 nm irradiation. Irradiation at 350 nm cross-links the exposed areas and the masked regions of polymer are removed by solvent washing (FIG. 3A,C). Conversely, irradiation at 254 nm results predominantly in oligomeric chains due to polymer scission and washing of the residual oligomers with suitable solvents results in the patterns shown in FIG. 3B,D. The depth of polymer etching is dependent on the time of irradiation, and under these conditions the polymer degraded to a depth of <40 nm. Using the 254 nm Rayonet source, this corresponds to a penetration of about 1 nm/min of irradiation. These results highlight the utility of this polymer system to fabricate complementary micropatterns using two different wavelengths. Confocal microscopic images of these micropatterns show similar micrometer-sized images. The height/depth profiles from the confocal microscope reveal complementary images resulting from 254 and 350 nm irradiations.

Fluorescence images of polymer films patterned with masks having 200 μm circular patterns proved that these patterns are not limited to the microscale but can be translated to feature sizes that are relevant for tissue engineering and cell biology applications. (The fluorescence is due to the coumarin polymer.)

The hydrolytic degradation of these coumarin polyesters were investigated by incubating thin films of the polymers in phosphate buffered saline (PBS, pH 7.4) for 10 weeks. During this time frame, CA11 showed a decrease in Mn from 11K to 6K. However, during the same time frame CAQ did not show any appreciable loss of molecular weight. This stability of CAQ can be attributed to the increased hydrophobicity due to the aromatic groups and the higher Mn relative to CA11.

Figure 4A:
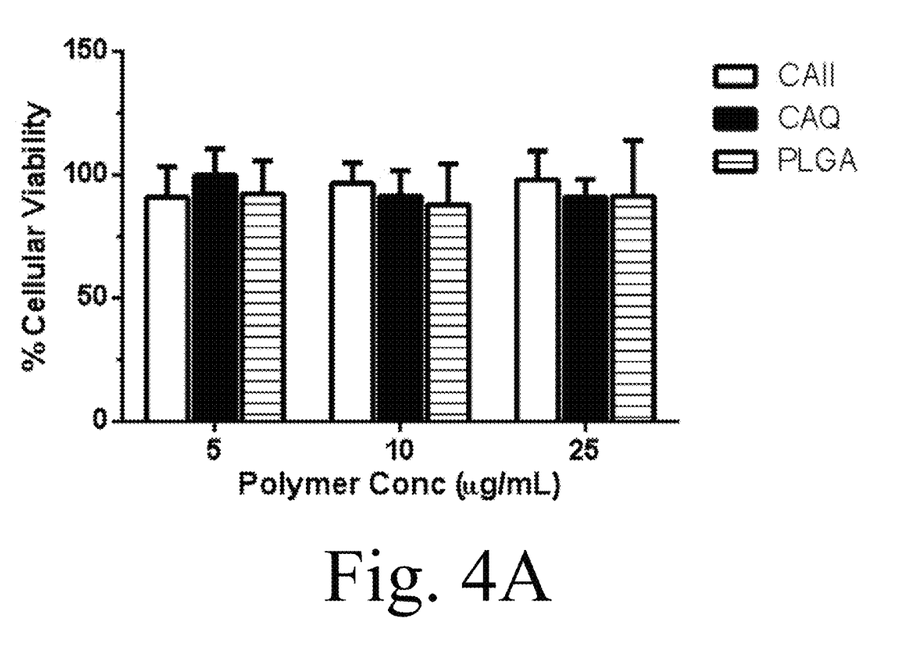
FIG. 4A provides a chart of a biocompatibility evaluation (mean±SD; n=4) of polymers 4 (CA11) and 5 (CAQ) based on cellular viability following incubation (37° C.; 24 h) with RAW 264.7 cells.

The biocompatibility assessment of the coumarin polyesters was evaluated in a macrophage cell line (RAW 264.7) exposed to varying concentrations of the polymers CA11 and CAQ dissolved in DMSO and added to the complete culture media. Data from 24 h cell viability, as determined by MTT assay, showed high cell viability for both polymers (FIG. 4A) and is comparable to poly(lactic acid-co-glycolic acid) (PLGA; 50:50), a commonly used biomaterial (p>0.05; FIG. 4A). Even at the highest polymer concentration tested (50 mg/mL), cellular viability remained above 90%. We also investigated the biocompatibility of microparticles of CA11 irradiated at 254 nm (30 min) and 350 nm (20 min). Under these conditions, photodegradation is maintained at a low concentration, which is a more likely representation of the in vivo conditions where the degraded polymer concentration will be much lower than the original polymer concentration.

Figure 4B:
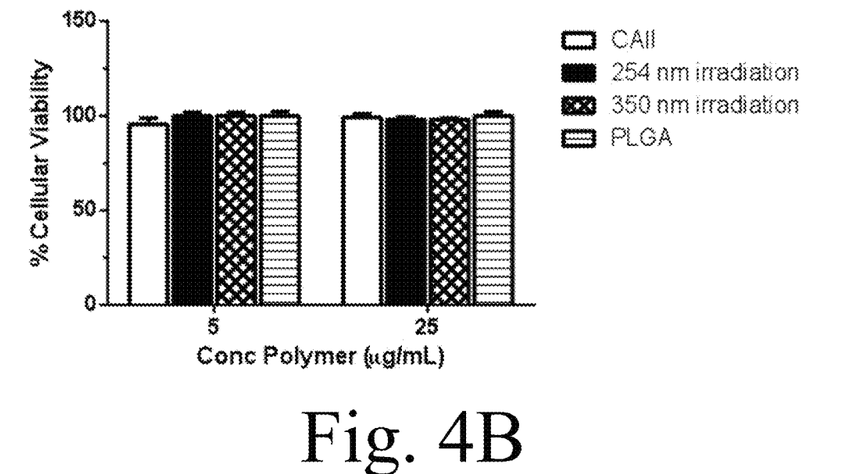
FIG. 4B provides a chart of a biocompatibility evaluation (mean±SD; n=7) Cellular viability of RAW 264.7 cells following incubation (37° C., 24 h) with photoirradiated CA11 polymer.

The biocompatibility of photoirradiated CA11 was examined by incubation of the products of microparticle photoirradiation (dissolved in DMSO and added to media) with RAW cells. These studies showed high cell viability for the photoirradiated products, which is comparable to the non-irradiated CA11 and also to PLGA (FIG. 4B; p>0.05).

Figure 5A:
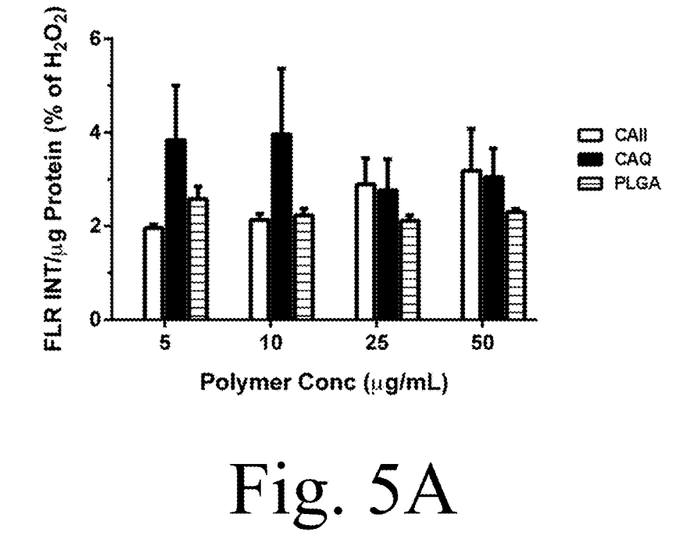
FIG. 5A provides a chart of a macrophage activation monitored by ROS production in RAW 264.7 cells after incubation (37° C., 24 h) with coumarin polyesters or PLGA.
Figure 5B:
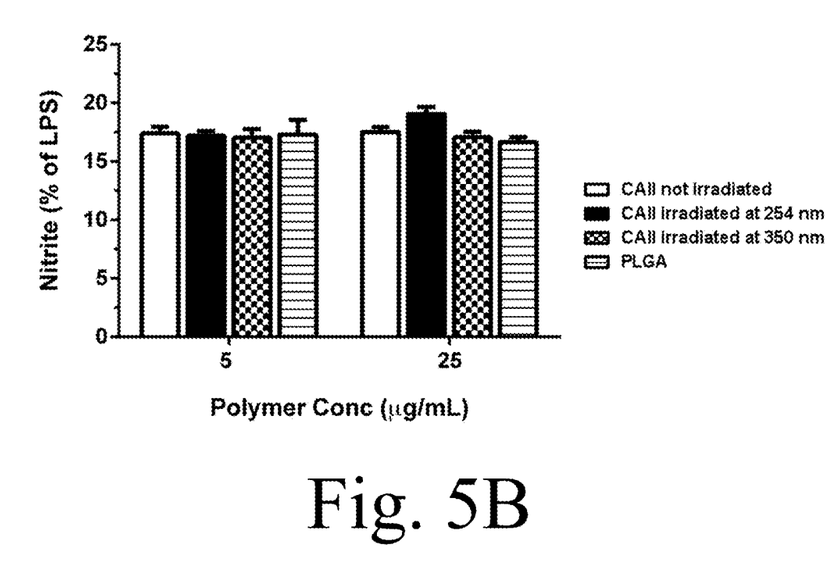
FIG. 5B provides a chart of the effects of photoirradiation of CA11 polymer on macrophage activation based on nitrite production after incubation (37° C., 24 h) with RAW 264.7 cells (mean±SD; n=7).

In related studies, macrophage activation of CA11 and CAQ was assessed based on production of reactive oxygen species (ROS) after incubation of varying concentrations of the polymers with RAW cells. At 24 h time points, ROS production in cells exposed to the polymers was comparable to untreated cells as well as to PLGA (p>0.05; FIG. 5A). Data points (mean±SD; n=4) are expressed as fluorescence intensity (FLR INT) normalized per microgram of protein. Each data point is plotted as a percentage of the positive control (hydrogen peroxide, 100 μM). ROS levels in polymer-treated cells were comparable to untreated control cells. Similarly, macrophage activation (monitored by nitrite production) of photoirradiated CA11 polymer was comparable to untreated control cells. The trend indicated that photoirradiation of CA11 polymer did not adversely affect the observed biocompatibility (p>0.05; FIG. 5B). (Each data point is plotted as a percentage of the positive control (LPS, 10 μg/mL). Nitrite levels in polymer-treated cells were comparable to untreated (control) cells.)

Having established the photodegradability of the polymers (4 & 5), we investigated whether these polymers are capable of forming nanoparticles and whether these photoresponsive nanoparticles would release embedded organic molecules upon light activation. Such studies are important to understand the limitations of the polymers for drug delivery applications. To demonstrate this, we chose a dye molecule (Nile Red, NR) to encapsulate within the polymer when it forms nanoparticles. Polymers 4 and 5 are mixed with 1 wt % dye in DMSO solution and the nanoparticles are obtained by adding this solution to water (3% EtOH) (Supporting Information). The size of the dye encapsulated nanoparticles was measured by dynamic light scattering (DLS). The average diameter of the nanoparticles were measured by dynamic light scattering (DLS) and show the particles to be of 220 nm (NR@CA11 nanoparticles) and 400 nm (NR@CAQ143 nanoparticles). Thus obtained nanoparticle solution was irradiated and the absorbance of the solution was monitored as a function of irradiation time. The data obtained clearly indicate the release of the dye molecule from both the polymers upon light activation at two different wavelengths (254 and 350 nm). As expected, the rate of release of the dye molecule was very high when irradiated at 254 nm light. The extensive backbone degradation of the polymers led to efficient release of the dye from the nanoparticles. Between the two polymers (4 and 5), we observed that the polymer 5 releases the dye much faster than polymer 4. In case of nanoparticles made from polymer 4, maximum amount of dye release was observed after being exposed to light for 150 seconds. However, it took only 45 seconds to see the maximum dye release from the nanoparticles that are made from polymer 5. This could be explained based on the rate of photocleavage reaction and photocrosslinking reaction observed in the solution irradiation. In the solution, when irradiated at 254 nm, we observed about 12-15% crosslinking in polymer 4 and 4-5% crosslinking in polymer 5 (due to the difference in the amount of coumarin in both polymers). In nanoparticle irradiation, the coumarin molecules located in much more closer environment with less translational freedom. Thus, there could be a competition between photocleavage and photocrosslinking reactions and depends on the mole % of the coumarin, which led to the difference in the rate of dye release from the polymers. On the other hand, irradiation at 350 nm wavelength resulted in very low release of dye from the nanoparticles. We assume that crosslinking at this wavelength decreases the rate of dye release from the nanoparticle core. Furthermore, the controlled dye release from the nanoparticles was demonstrated as a function of the overall power of incident light. There is the limitation that these materials can only be used in applications, which are accessible to 254 or 350 nm light, and efforts are currently underway in our laboratory to extend the absorption maximum to the visible region.

In conclusion, the synthesis, characterization, and photochemical behavior of two novel coumarin-based polyesters are reported here. These photoresponsive polymers exhibit dual photoresponsive properties: cross-linking upon 350 nm irradiation and polymer chain scission and un-cross-linking at 254 nm irradiation. The photochemical behavior was studied by ssNMR, IR, UV, and GPC. In addition, we have shown that complementary micropatterned surfaces can be fabricated by irradiation at 350 and 254 nm. These coumarin polyesters are mechanically robust and stable in the absence of light. Preliminary studies with macrophage RAW 267.4 cells show that these polymers and their irradiation products are biocompatible, and the cell viability is comparable to that for PLGA. The properties of these polymers may be useful for printing 2D and 3D devices and for controlled release devices.

Various modifications and alterations that do not depart from the scope and spirit of this invention will become apparent to those skilled in the art. This invention is not to be duly limited to the illustrative embodiments set forth herein.

What is claimed is:

1. A polymer comprising a polyurethane or a polyester that includes as part of the polymer backbone a coumarin unit or a coumarin derivative unit defined by the formula:

where each $R^2$ is individually a hydrogen atom, a bromine atom, an iodine atom, or a methoxy group; $R^3$ is a hydrocarbon group; $R^4$ is a hydrocarbon group; Y is an oxygen atom or a nitrogen atom with an organic substitution; Z is selected from ester groups or urethane groups; and α is an oxygen atom or a sulfur atom; a coumarin unit or a coumarin derivative unit that is crosslinked to a second coumarin unit or coumarin derivative unit defined by the formula:

where each $R^2$ is individually a hydrogen atom, a bromine atom, an iodine atom, or a methoxy group; each $R^3$ is independently a hydrocarbon group; each $R^4$ is independently a hydrocarbon group; each Y is independently an oxygen atom or a nitrogen atom with an organic substitution; each Z is independently selected from ester groups or urethane groups; and each α is independently an oxygen atom or a sulfur atom; or a combination thereof.

2. The polymer of claim 1, where the coumarin unit or the coumarin derivative unit is defined by the formula:

where each $R^2$ is individually a hydrogen atom, a bromine atom, an iodine atom, or a methoxy group; $R^3$ is a hydrocarbon group; $R^4$ is a hydrocarbon group; Y is an oxygen atom or a nitrogen atom with an organic substitution; Z is selected from ester groups or urethane groups; and α is an oxygen atom or a sulfur atom.

3. The polymer of claim 1, where the coumarin unit or the coumarin derivative unit is defined by the formula:

4. The polymer of claim 1, where the coumarin unit or the coumarin derivative unit is crosslinked to a second coumarin unit or coumarin derivative unit, and where the crosslink is defined as:

where each $R^2$ is individually a hydrogen atom, a bromine atom, an iodine atom, or a methoxy group; each $R^3$ is independently a hydrocarbon group; each $R^4$ is independently a hydrocarbon group; each Y is independently an oxygen atom or a nitrogen atom with an organic substitution; each Z is independently selected from ester groups or urethane groups; and each α is independently an oxygen atom or a sulfur atom.

5. A method of preparing the polymer of claim 1 comprising:
reacting a diisocyanate or a dicarboxylic acid with a photoreactive coumarin monomer defined by the formula:

where each $R^2$ is individually a hydrogen atom, a bromine atom, an iodine atom, or a methoxy group; $R^3$ is a hydrocarbon group; Y is an oxygen atom or a nitrogen atom with an organic substitution; and α is an oxygen atom or a sulfur atom.

6. The method of claim 5, where the photoreactive coumarin monomer is reacted with a diisocyante defined by the formula where $R^4$ is a hydrocarbon group.

7. The method of claim 5, where the diisocyante is selected from the group consisting of hexamethylene diisocyanate and 1,3-phenylene diisocyanate.

8. The method of claim 5, where the photoreactive coumarin monomer is reacted with a dicarboxylic acid defined by the formula where $R^4$ is a hydrocarbon group.

9. The method of claim 5, where the dicarboxylic acid is selected from the group consisting of succinic acid, glutaric acid, adipic acid, pimelic acid, suberic acid, sebacic acid, protected glutamic acids, protected aspartic acids, terepthalic acid, pthalic acid and isopthalic acid.

* * * * *